United States Patent
Wang et al.

(10) Patent No.: US 11,398,023 B2
(45) Date of Patent: Jul. 26, 2022

(54) SYSTEM AND METHOD FOR CONCURRENT VISUALIZATION AND QUANTIFICATION OF WALL SHEAR STRESS IN BLOOD VESSELS

(71) Applicant: KONINKLIJKE PHILIPS N.V., Eindhoven (NL)

(72) Inventors: Shiying Wang, Melrose, MA (US); Sheng-Wen Huang, Ossining, NY (US); Hua Xie, Cambridge, MA (US); Francois Guy Gerard Marie Vignon, Andover, MA (US); Keith William Johnson, Lynnwood, WA (US); Liang Zhang, Issaquah, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 218 days.

(21) Appl. No.: 16/608,284

(22) PCT Filed: May 4, 2018

(86) PCT No.: PCT/EP2018/061611
§ 371 (c)(1),
(2) Date: Oct. 25, 2019

(87) PCT Pub. No.: WO2018/202899
PCT Pub. Date: Nov. 8, 2018

(65) Prior Publication Data
US 2020/0126219 A1    Apr. 23, 2020

Related U.S. Application Data

(60) Provisional application No. 62/501,448, filed on May 4, 2017.

(51) Int. Cl.
*G06T 7/00* (2017.01)
*G16H 30/20* (2018.01)
(Continued)

(52) U.S. Cl.
CPC .............. *G06T 7/0012* (2013.01); *A61B 8/06* (2013.01); *A61B 8/0883* (2013.01);
(Continued)

(58) Field of Classification Search
CPC ......... G06T 7/0012; G06T 2207/10132; G06T 2207/20084; G06T 2207/30101;
(Continued)

(56) References Cited

U.S. PATENT DOCUMENTS 6,654,628 B1    11/2003    Silber et al.
8,934,690 B2    1/2015    Mohamed
(Continued)

FOREIGN PATENT DOCUMENTS

WO    2014190541 A1    12/2014
WO    2016065161 A1    4/2016

OTHER PUBLICATIONS

Akagawa et al: "Two-Dimensional Blood Flow Vector and Wall Shear Stress of Carotid Artery Obtained With Dual-Angle Doppler Method"; 2016 IEEE International Ultrasonics Symposium, Sep. 2016, pp. 1-4.
(Continued)

*Primary Examiner* — Emily C Terrell
*Assistant Examiner* — Molly Delaney

(57) ABSTRACT

A system according to the present disclosure may include a display unit, a processor communicatively coupled to the display unit and to an ultrasound imaging apparatus for generating an image from ultrasound data representative of a bodily structure and fluid flowing within the bodily structure. The processor may be configured to generate vector field data including axial and lateral (or transverse) velocity components of the fluid flowing within the bodily structure, calculate velocity profiles for a plurality of locations along a wall of the bodily structure based on the axial and lateral
(Continued)

velocity components, generate wall shear stress (WSS) visualization data based, at least in part, on the velocity profiles, and cause the display unit to concurrently display the image including the bodily structure overlaid with the WSS visualization data.

16 Claims, 9 Drawing Sheets

(51) Int. Cl.
*A61B 8/06* (2006.01)
*G16H 50/20* (2018.01)
*A61B 8/08* (2006.01)
*A61B 8/00* (2006.01)

(52) U.S. Cl.
CPC ............ *A61B 8/0891* (2013.01); *A61B 8/463* (2013.01); *A61B 8/485* (2013.01); *A61B 8/5223* (2013.01); *G16H 30/20* (2018.01); *G16H 50/20* (2018.01); *G06T 2207/10132* (2013.01); *G06T 2207/20084* (2013.01); *G06T 2207/30101* (2013.01)

(58) Field of Classification Search
CPC .......... G16H 30/20; G16H 50/20; A61B 8/06; A61B 8/0883; A61B 8/0891; A61B 8/463; A61B 8/485; A61B 8/5223
See application file for complete search history.

(56) References Cited

U.S. PATENT DOCUMENTS

| | | | |
|---|---|---|---|
| 9,462,954 B2 | 10/2016 | Mihalef et al. | |
| 2009/0214097 A1* | 8/2009 | Mohamed | G06T 7/0012 382/131 |
| 2011/0245672 A1* | 10/2011 | Tamura | G01S 7/52036 600/443 |
| 2011/0275936 A1 | 11/2011 | Cho et al. | |
| 2012/0072190 A1 | 3/2012 | Sharma et al. | |
| 2012/0283564 A1* | 11/2012 | Ebbini | A61B 8/06 600/439 |
| 2013/0289408 A1 | 10/2013 | Tomohiko et al. | |
| 2016/0203288 A1 | 7/2016 | Meng et al. | |
| 2017/0296140 A1* | 10/2017 | Ebbini | A61B 8/06 |
| 2018/0161011 A1* | 6/2018 | Owen | A61B 8/485 |
| 2018/0235578 A1* | 8/2018 | Berger | A61B 8/5207 |
| 2020/0054217 A1* | 2/2020 | Parker | A61B 5/7239 |
| 2021/0236086 A1* | 8/2021 | Du | A61B 8/485 |

OTHER PUBLICATIONS

Itatani et al: "Intraventricular Flow Velocity Vector Visualization Based on the Continuity Equation and Measurements of Vorticity and Wall Shear Stress"; Japanese Journal of Applied Physics, vol. 52, No. 7S, Jul. 2013, pp. 07HF16-1-07HF16-07HF16-6.

Brands et al: "A Noninvasive Method to Estimate Wall Shear Rate Using Ultrasound"; Ultrasound in Med. & Biol. vol. 21, No. 2, pp. 171-185, 1995.

Sengupta et al: "Emerging Trends in CV Flow Visualization"; JACC: Cardiovascular Imaging, vol. 5, No. 3, Mar. 2012, pp. 305-316.

Shimizu et al: "Wall Shear Stress Measurement Method Based on Novel Flow Model Near Vascular Wall in Echography"; Symposium on Ultrasonic Electronics, vol. 37, pp. 3P5-3P5, Nov. 2016.

Markl et al: "In Vivo Wall Shear Stress Distribution in the Carotid Artery" Effect of Bifurcation Geometry, Internal Artery Stenosis, and Recanalization Therapy; Circulation, Cardiovascular Imaging, Vo. 3, No. 6, pp. 647-655, 2010, Nov. 2010.

Malek et al: "Hemodynamic Shear Stress and Its Role in Atherosclerosis": JAMA, Dec. 1999, vol. 282, No. 21, pp. 2035-2042.

Reneman et al: "Wall Shear Stress-An Important Determinant of Endothelial Cell Function and Structure-In the Arterial System In Vivo"; Journal of Vascular Research, 2006, VO. 43, pp. 251-269.

Ross:"Atherosclerosis-An Inflammatory Disease"; New England Journal of Medicine, vol. 340, No. 2, pp. 115-126.

PCT/EP2018/061611, Written Opinion and ISR, dated Aug. 17, 2018 24 Page Document.

* cited by examiner

SYSTEM AND METHOD FOR CONCURRENT VISUALIZATION AND QUANTIFICATION OF WALL SHEAR STRESS IN BLOOD VESSELS

CROSS-REFERENCE TO PRIOR APPLICATIONS

This application is the U.S. National Phase application under 35 U.S.C. § 371 of International Application No. PCT/EP2018/061611, filed on May 4, 2018, which claims the benefit of U.S. Provisional Patent Application No. 62/501,448, filed on May 4, 2017. These applications are hereby incorporated by reference herein.

TECHNICAL FIELD

This application pertains to ultrasound imaging and more specifically to systems and methods for concurrent visualization and quantification of wall shear stress of bodily structures, such as blood vessels.

BACKGROUND

Atheroma is the accumulation of degenerative material in the vessels of the vasculature, and often leads to atherosclerosis (which is the hardening of vessel walls). Atherosclerosis is one of the worldwide leading causes of death. Studies have identified that wall shear stress (WSS) is an important determinant of endothelial cell function. WSS is the tangential friction force applied on endothelial cells of a blood vessel wall as the result of blood flow. Regular arterial-level WSS (equal to or higher than 15 dyne/cm$^2$) induces an atheroprotective gene expression profile, while low WSS (less 4 dyne/cm$^2$) stimulates an atherogenic phenotype. Thus, screening and monitoring of WSS in blood vessels can provide risk estimation of plaque development. Several non-invasive techniques have been developed to measure WSS including the use of MRI and ultrasound.

SUMMARY

The present invention provides systems and methods for concurrent visualization and quantification of WSS. Powered by angle-independent velocity estimation techniques, examples according to the present disclosure may provide solutions for visualizing in an intuitive manner the wall shear stress distribution along the wall of a bodily structure, such as a blood vessel and to obtain spatiotemporal information about the WSS along the wall. Additionally, the examples herein may provide an intelligent, risk prediction tool which may improve diagnostic efficiency.

A system according to the present disclosure may include a display unit, a processor communicatively coupled to the display unit and to an ultrasound imaging apparatus for generating an image from ultrasound data representative of a bodily structure and fluid flowing within the bodily structure. The processor may be configured to generate vector field data including axial and lateral (or transverse) velocity components of the fluid flowing within the bodily structure, calculate velocity profiles for a plurality of locations along a wall of the bodily structure based on the axial and lateral velocity components, generate wall shear stress (WSS) visualization data based, at least in part, on the velocity profiles, and cause the display unit to concurrently display the image including the bodily structure overlaid with the WSS visualization data. In some examples, the system described herein may be embodied in an ultrasound imaging systems which includes the imaging apparatus and the display and processor described herein for generating and displaying B-mode images and the WSS visualization data as described herein. In some examples, the generation and display of images may be performed in real-time while ultrasonically imaging the bodily structure.

In some embodiments, the processor may be configured to encode in color a WSS value at each of the plurality of locations along the wall to generate the WSS visualization data. The WSS visualization data may be provided in the form of a color map which may be overlaid onto a grayscale image of the anatomy (i.e., an echo or B-mode image). This type of a displayed image (or simply display) may be referred to as a duplex mode image as it provides imaging data from two imaging modes, namely B-mode imaging and WSS imaging. In some embodiments, the processor may be further configured to generate a graphical representation of the vector field data (e.g., a pathlet-based or other type of vector map) and cause the display unit to display the graphical representation of the vector field data concurrently with, for example as an overlay onto, the B-mode image, which also includes the WSS visualization data. This type of a displayed image (or simply display) may be referred to as a triplex mode image as it provides imaging data from three imaging modes, namely B-mode, vector flow imaging (VFI), and WSS imaging. Examples of graphical representation of the vector field data in the form of a pathlet-based visualization of the vector field data are described in further details below; however, other types of vector flow imaging techniques may be used, such as fixed- or free-arrow based techniques. In any of the examples herein, the image data from each mode in the overlay images (e.g., duplex or triplex mode images) may be synchronously dynamically updated in real time. For example, in the case of a duplex display, the B-mode image data may be displayed as a temporal sequence of a plurality of B-mode image frames, which may be acquired in real time or retrieved from memory (i.e., a cineloop) and the WSS visualization data (e.g., WSS color map) may also be displayed/overlaid as a temporal sequence of a plurality of corresponding WSS image data frames, which may be generated in real time (from real-time echoes) or retrieved from memory.

The plurality of locations for which WSS values are calculated is also referred to as the WSS region of interest (ROI). In some embodiments, the processor may be configured to determine the plurality of locations along the wall of the bodily structure for which WSS values are to be calculated (i.e., the WSS ROI) automatically from the ultrasound imaging data. For example, this may be done by using image processing techniques such as image segmentation to identify the wall of the bodily structure and WSS values may be calculated for the entire length of vessel wall in any given image frame. In some examples, the processor may re-define the WSS ROI to a sub-region which is determined to include clinically relevant WSS values and may cause color-coded WSS information to be displayed only for this sub-region. In yet further examples, the processor may be configured to select the plurality of locations along the wall and for which WSS values are to be calculated (i.e., the WSS ROI) responsive to user input. For example, the WSS ROI may be user defined, such as responsive to the user selecting, via a user interface, a plurality of points on the displayed image to trace the outline of the vessel wall and/or by drawing, via the user interface, the boundary of the WSS ROI on the display.

In some examples, the graphical representation of the vector field data may include a vector map including a flow mask layer that defines a sub-region corresponding to the vector field data (also referred to as flow region) and a vector visualization layer illustrating at least partial trajectories of velocity vectors in the flow region. In some embodiments, the boundary of the flow mask layer may be user-defined, such as by the user drawing a polygon or other shaped outline on a display of the anatomy (e.g., a B-mode image). In other embodiments, the boundary of the flow mask layer may be automatically determined (e.g., by the processor) for example based on a region of detected flow. In some example, the region of detected flow may vary from frame to frame such as due to variances in the amount of flow or flowrate at different times of the cardiac cycle, and thus the boundary of the flow mask layer may correspondingly vary from frame to frame based on the available vector field data in each temporally consecutive frame. In yet other examples, the boundary of the flow mask layer may be automatically determined (e.g., by the processor) using image processing techniques, such as image segmentation, to identify the walls of the bodily structure and thus defining the flow region to a region within the walls of the bodily structure. Combination of these methods or other methods for defining the flow region may be used.

In some embodiments, the WSS visualization data may additionally or alternatively include risk values that are determined based on the WSS values. For example, the processor may be configured to determine plaque-development risk estimates based, at least in part, on the WSS values. This quantitative measure of risk may be visually presented on a display concurrently with at least the B-mode image data, for example as an overlay on the imaged anatomy in a similar manner as the overlay of a WSS color map. In some embodiments, discrete risk value or a subset thereof, such as the critical risk values, may be displayed on the same image with the WSS color map at their corresponding location, for example adjacent to one or more locations of the wall which exhibit high risk for plaque development. In other embodiments, a color map of the risk values may be displayed as an overlay onto the anatomy image instead of the WSS color map. In some embodiments, two duplex mode images, one including a WSS color map overlaid on a corresponding B-mode image and another including a color map of the corresponding risk values overlaid on the corresponding B-mode background image, may be displayed side by side. The image data associated with each imaging mode includes in the displays may be dynamically and synchronously updated across all displayed images.

Plaque-development risk estimates may be determined, in some examples, using a thresholding process, which may in some cases, be enhanced by machine learning. For example, the processor may be configured to designate one or more locations along the wall that are associated with WSS values below a first or low WSS threshold (e.g., below 4 dyne/cm$^2$) as high-risk, while locations associated with WSS values above a second or regular WSS threshold (e.g., above 15 dyne/cm$^2$) as low-risk. Any locations having intermediate WSS values may be designated as medium risk. Locations designated as high risk may be color coded by a given color such as pink, and locations designated as low risk may be color coded by another color such as gray. The locations designated as medium risk may be encoded in yet another, third color or they may be encoded based on a gradient of color blending the low risk to the high risk colors. As will be further described, the thresholding processes may be augmented or enhanced by machine learning. For example, the WSS thresholds may be obtained from a neural network which is trained, using a set of training samples (e.g., patient screening results) obtained from a diverse set of subject, to determine the appropriate thresholds. As such, the robustness of the risk assessment mode may be enhanced by taking into account existing intra-subject and inter-subject variabilities in threshold definitions for atherosclerosis-prone site identification.

In yet further examples, the visualization system described herein may be configured to provide additional spatiotemporal information by displaying the calculated WSS information as a function of time. For example, the processor may be further configured to display a graphical representation of WSS values associated with some or all of the plurality of locations along the wall as a function of time. In some examples, this graphical representation, also referred to as WSS M-mode display or image, may provide a color coded display of the WSS values for a section or the full length of the wall as a function of time. Alternatively, temporal variability of the WSS values in the WSS M-mode display may be tracked using curves or traces, rather than color encoding. The WSS M-mode display may be provided concurrently (e.g., in a side-by-side arrangement) with any of the duplex or triplex mode images described herein, in which cases the WSS M-mode image may also be synchronously updated with the image data in the other displayed images. In some cases, a cardiac cycle indicator may accompany the WSS M-mode display or image. The cardiac cycle indicator may be provided in the form of an ECG signal trace, which may be displayed adjacent to the M-mode image (e.g., below the time axis) and synchronized therewith. With this additional image component, the characteristic events, including switch in WSS direction and peak WSS can be easily visualized thus providing rich spatiotemporal WSS information to the clinical that may enhance diagnostic efficiency.

A method for displaying ultrasound imaging data may include generating an image from ultrasound data representative of a bodily structure and fluid flowing within the bodily structure, generating vector field data including axial and lateral velocity components of the fluid flowing within the bodily structure, calculating velocity profiles for a plurality of locations along a wall of the bodily structure based on the axial and lateral velocity components, generating wall shear stress (WSS) visualization data based, at least in part, on the velocity profiles, and concurrently displaying the image including the bodily structure with the WSS visualization data. In some embodiments of the method, the generating of WSS visualization data may include generating a color map of WSS values at each of the plurality of locations along the wall and wherein the concurrently displaying the image with the WSS visualization data includes overlaying the color map of WSS values onto a B-mode image of the bodily structure In some embodiments, the method may further include generating a graphical representation of the vector field data, and concurrently displaying the graphical representation of the vector field data with the image including the bodily structure and the WSS visualization data. The generating of a graphical representation of the vector field data may include generating a pathlet-based visualization of the vector field data. In some embodiments of the method, the generating of WSS visualization data includes calculating WSS values for each of the plurality of locations along the wall and generating a color map of risk estimates determined based, at least in part, on the WSS values, and the concurrently displaying of an image with the WSS visualization data may include overlaying the color map of risk estimates onto a B-mode image of the bodily structure. In some embodiments, the method may further include displaying a graphical representation of the WSS values as a function of time. In some embodiments, the graphical representation of the WSS values as a function of time may be displayed synchronously with a corresponding ECG signal trace. In embodiments according to the present disclosure, the image including the bodily structure (e.g., B-mode image) and the WSS visualization data may be updated in real-time.

Any of the methods in accordance with the present disclosure, or steps thereof, may be embodied in non-transitory computer-readable medium comprising executable instructions, which when executed may cause a processor, such as a processor of medical imaging system, to perform the method or steps embodied therein.

DESCRIPTION

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

In this disclosure, a method for simultaneous visualization and quantification of WSS such as using triplex B-mode and anatomical M-mode displays is proposed. Existing systems and methods for measuring WSS do not provide the ability to concurrently visualize and accurately quantify WSS. Typically, color-coded WSS is superimposed on a B-mode image providing only a spatial distribution of WSS. However, WSS may change significantly with time (e.g., during each cardiac cycle), the spatiotemporal distribution of WSS may provide additional clinically useful information.

Figure 7:
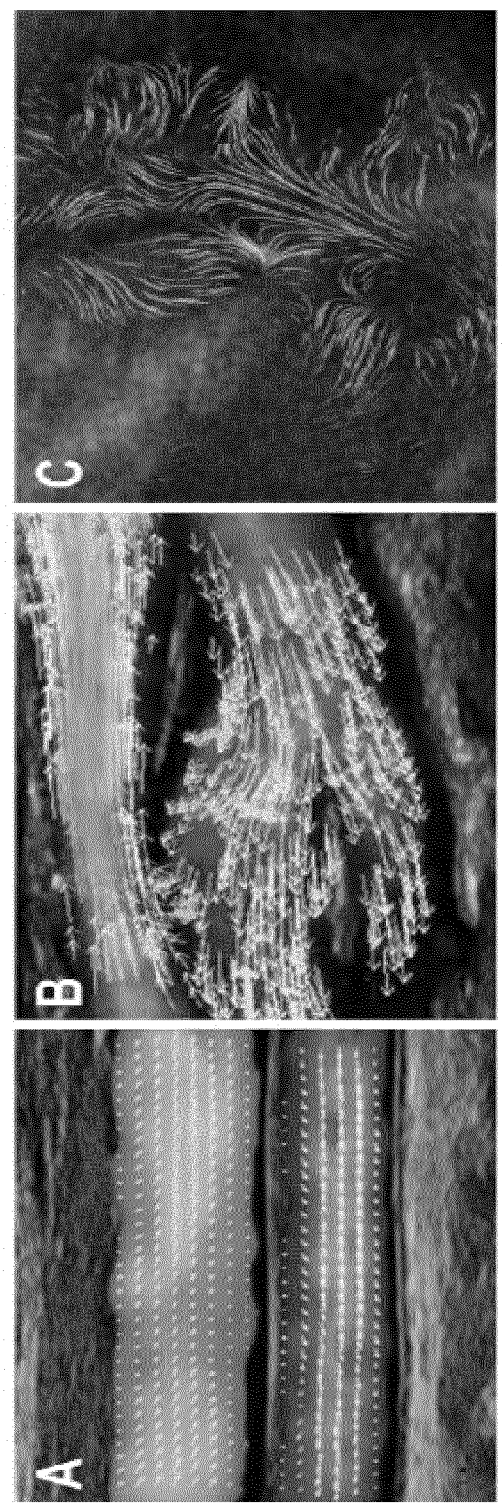
FIGS. 7A, 7B, and 7C show additional examples of vector flow imaging techniques for generated visual representations of the vector field data in systems according to the present disclosure.

More accurate calculation of WSS than with existing techniques may be achieved by angle-independent vector flow imaging. In contrast to conventional Doppler ultrasound, which only allows velocity estimation along the axial direction, new vector flow imaging (VFI) techniques have been introduced to allow multi-directional velocity estimations. Vector flow imaging can be used to visualize and quantify complex blood flow measurements in cardiovascular applications for better diagnosis of stenosis and other conditions of the vascular system. Example VFI techniques include fixed-arrow-based (see FIG. 7A), free-arrow-based (see FIG. 7B), and pathlet-based visualization (see FIG. 7C). In the case of fixed-arrow-based visualization, the magnitude of flow velocity is encoded as color intensity, and is proportional to the length of the arrow. The direction of flow velocity is shown both by the arrow and color. The tail of the arrow is fixed in space. In free-arrow-based visualization, free arrow is used to dynamically track the blood flow. The magnitude of flow velocity is color encoded, and is proportional to the length of the arrow. The direction of flow velocity is indicated by the arrow. A streamline may be defined as a family of curves that are instantaneously tangent to the velocity vector of the flow, and a pathline can be defined as a family of trajectories that the flow particles would faithfully follow during flow.

Figure 5:
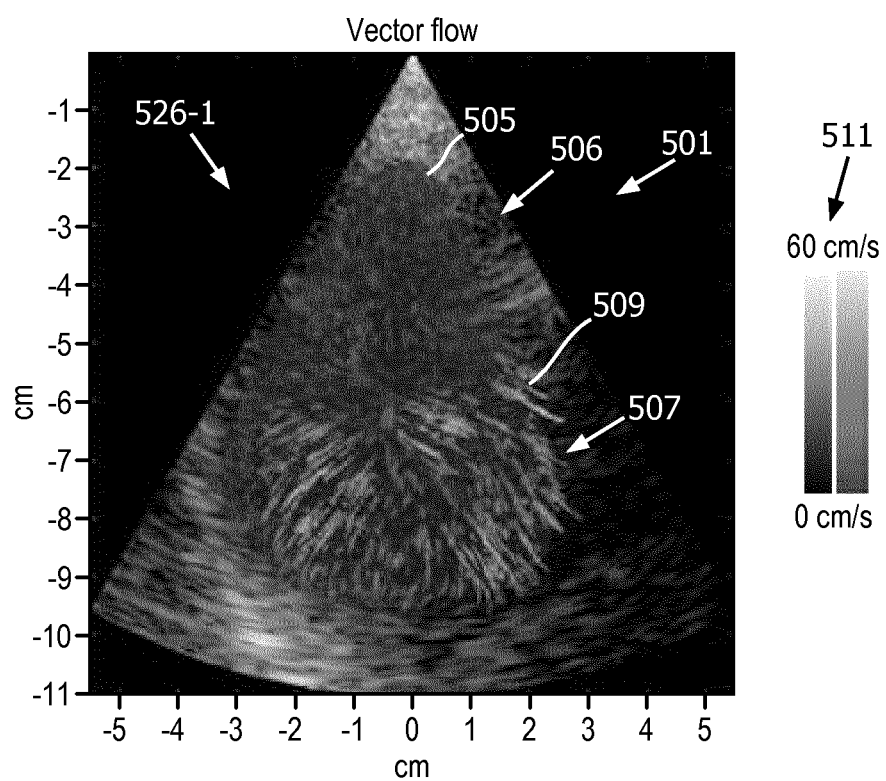
FIG. 5 is an ultrasound image illustrating a pathlet-based vector flow imaging technique for visualizing the blood flow pattern within the left ventricle of a human heart.
Figure 6:
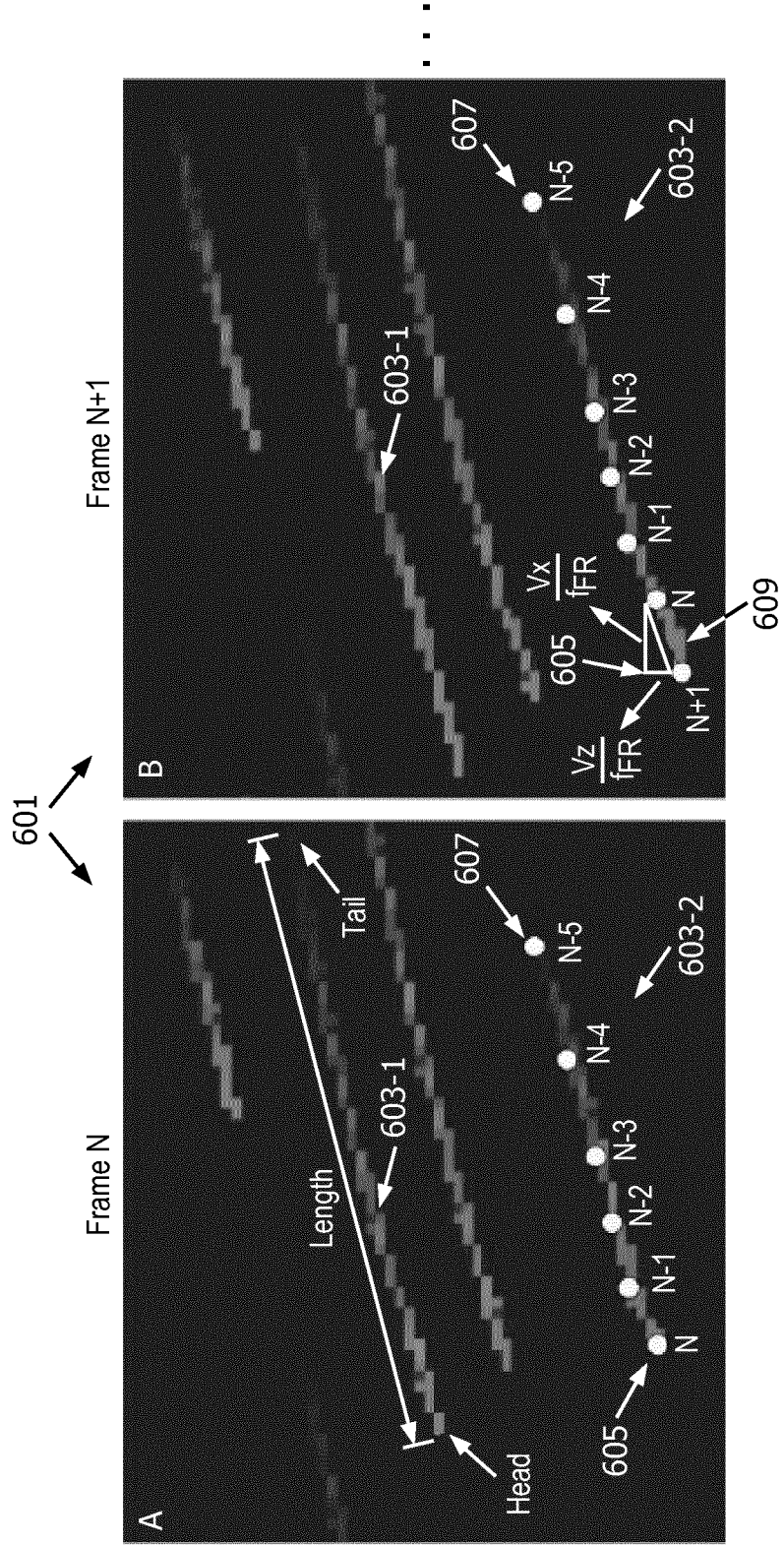
FIG. 6 shows an illustration of a portion of two consecutive frames of ultrasound image data and a technique for updating the pathlet-based information in the frames.

For pathlets-based visualization (e.g., as shown in FIGS. 5 and 6 and described further below), dynamic curve tracing of the flow trajectory is achieved by curved pathlets. Pathlets can be seen as the short, frontal segments or parts of the pathlines, that start to fade out when distance from the tip exceeds a given threshold, which is defined as the pathlet length. The magnitude of flow velocity is color encoded, and is proportional to the length of the pathlets. The direction of flow velocity is indicated by the moving direction of pathlets. Overall, among the three visualization methods, pathlet-based visualization is generally the most intuitive method with potential to replace the other visualization methods for VFI.

Example systems and methods in accordance with the present disclosure may enable a user to intuitively visualize clinically relevant information associated with estimated WSS values, such as plaque-development risk, and may thus provide, in an automatic and intelligent manner, an early warning technique that may enhance diagnostic efficiency and improve overall patient care.

Figure 1:
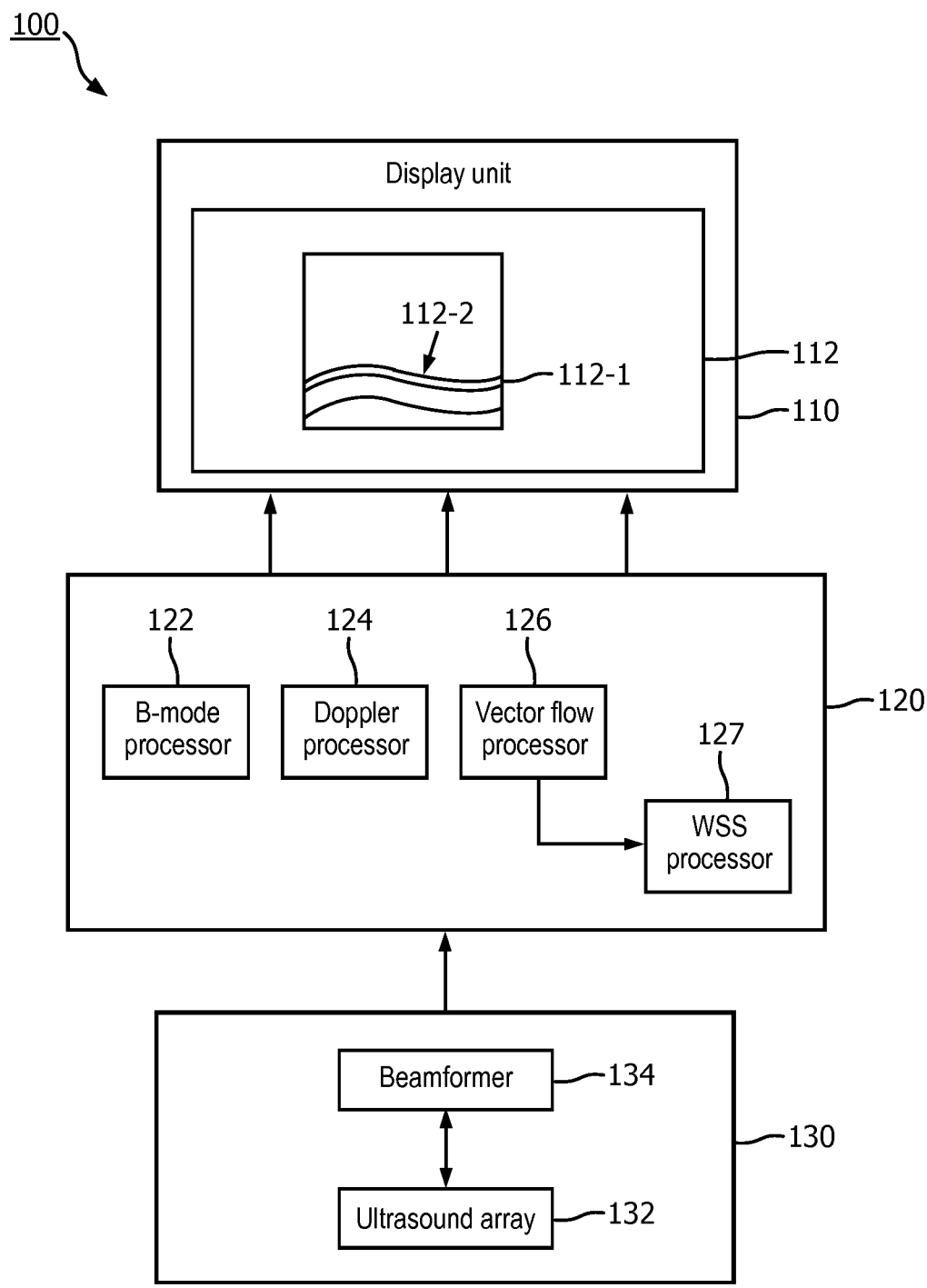
FIG. 1 is block diagram of a visualization and quantification system in accordance with the present disclosure.

In accordance with some examples herein, system for visualization and quantification of ultrasound image data may include a display unit and a processor communicatively coupled to the display unit. FIG. 1 shows a system for visualization and quantification of ultrasound imaging data in accordance with some examples of the present disclosure. For example, referring to FIG. 1, the system 100 may include a display unit 110, which may be implemented using any type of suitable display technology such as passive or touch-sensitive LCD, LED, or OLED technologies. The system 100 may also include a processor 120 which is communicatively coupled to the display unit 110 and to an ultrasound imaging apparatus 130 for generating an image 112 from ultrasound data. The image 112 may be representative of a bodily structure and fluid flowing within the bodily structure.

The ultrasound imaging apparatus 130, also referred to herein as ultrasound scanner, may include an ultrasound array 132 that may be housed in an external or an intravascular probe, and a beamformer 134, which may operate under the control of an imaging controller to direct ultrasound beams and receive ultrasound echoes from a subject (e.g., a patient) using the ultrasound array 132, which are then beam-formed and transmitted to one or more processors for further processing and image generation. In some embodiments, the processor 120 and/or the display unit 110, or components thereof (such as one or more of the processors 122, 124, and 126), may be integrated with the ultrasound imaging apparatus 130, which may for example be any of the ultrasound imaging system, such as the SPRAQ or the EPIQ ultrasound system, provided by PHILIPS. In some examples, the processor 120 may additionally or alternatively be configured to receive ultrasound imaging data, for example imaging data from an imaging session performed prior to visualization and quantification of the data by a clinician, and which has been stored in memory (e.g., memory storage device of a picture archiving and communication system (PACS)) for later access by the processor 120.

The processor 120 may be configured to generate ultrasound imaging data associated with two or more imaging modes (e.g., B-mode, Doppler imaging, Vector Flow imaging, etc.) for display on the display unit 110. To that end, the processor may include a B-mode processor 122 configured to generate B-mode images and a Doppler processor 124 configured to generate Doppler images (e.g., color-flow Doppler, spectral Doppler, and power Doppler such as Color Power Angio (CPA) images). In some examples, images may be displayed as overlays of imaging data obtained from multiple imaging modes. For example in duplex (e.g., B-mode/Doppler) imaging, a gray-scale image of the anatomy (i.e., a B-mode image) may be overplayed with color-flow Doppler data to provide, for example, a color-flow Doppler image.

In some embodiments, the processor 120 may be configured to generate vector field data including axial and lateral velocity components of the fluid flowing within the bodily structure. To that end, the processor 120 may include a vector flow processor 126 configured to generate angle-independent velocity estimates from the beamformed RF signals received from the imaging apparatus 130. The processor 120 may be further configured to generate vector flow imaging (VFI) data based on the vector field data, which data may be overlaid on background B-mode images similar to B-mode/Doppler duplex imaging.

The processor 120 may be further configured to calculate velocity profiles for a plurality of locations along a wall of the bodily structure based on the axial and lateral velocity components generated by the vector flow processor 126 and may be further configured to generate wall shear stress (WSS) visualization data based, at least in part, on the velocity profiles, as will be further described. For example, the vector flow processor 126 may include or be communicatively coupled to a WSS processor 127 configured to generate WSS values, risk estimates, and/or visualization data based on the WSS values and/or risk estimates. The processor 120 which is in communication with display unit 110 may cause the display unit 120 to concurrently display a sequence of frames of B-mode image data 112-1 including the bodily structure overlaid with a corresponding sequence of frames of the WSS visualization data 112-2. In some embodiments, the system 100 may be coupled to or part of the imaging apparatus and thus configured to generate images for display in real-time (e.g., while imaging the bodily structure to acquire the RF signals). In other examples, the system 100 may additionally or alternatively be coupled to a persistent storage device (e.g., PACS) and one or more of the images may be generated from stored image data. In some embodiments, the functionality of one or more of the processors (e.g., B-mode processor 122, Doppler processor 124, and vector flow processor 126) of system 100 may be integrated into a single or a fewer number of processors such as a specially programmed CPU or GPU operable to perform the functions of these processor described herein.

Figure 2:
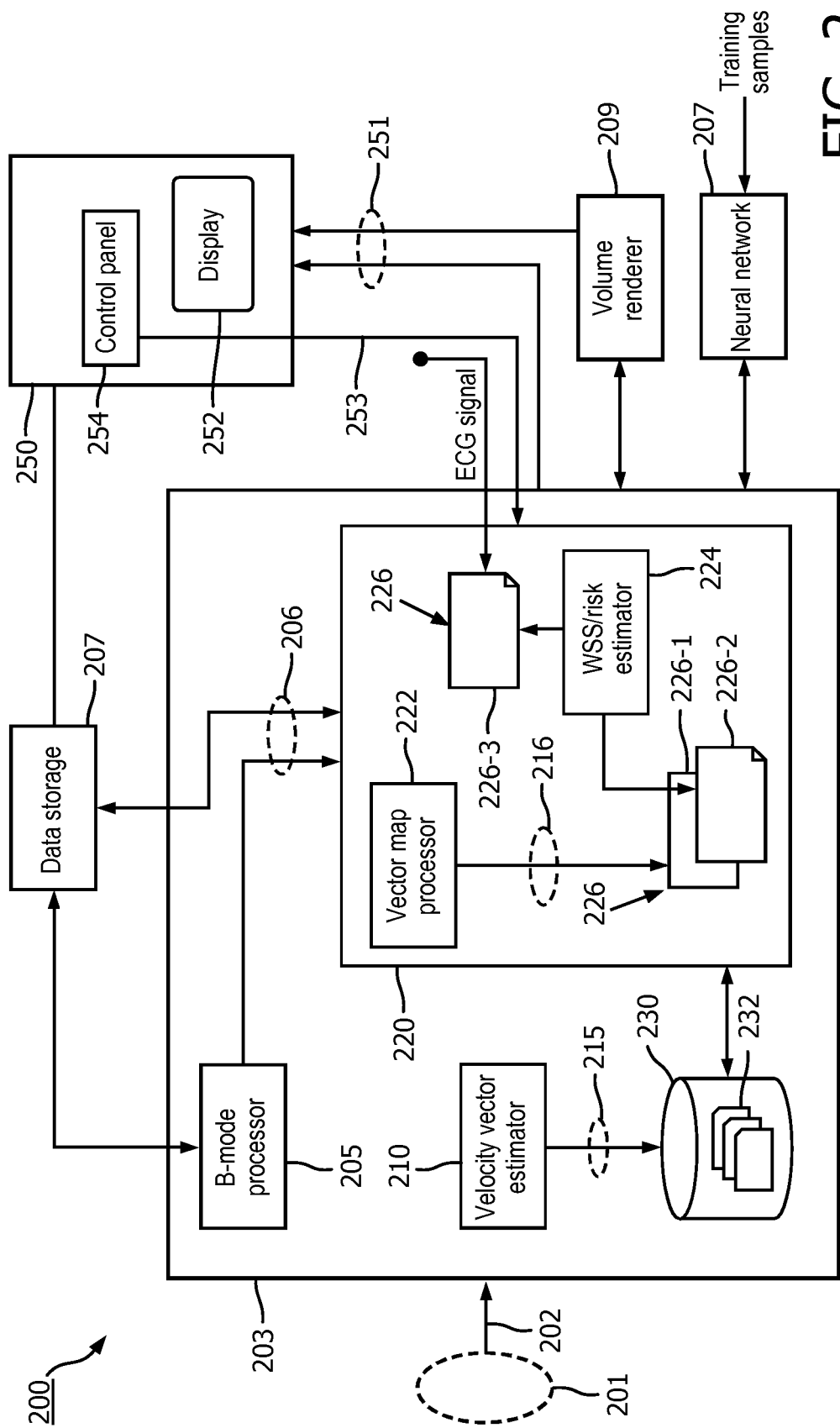
FIG. 2 is a block diagram of a visualization and quantification system in accordance with further examples of the present disclosure.
Figure 3A:
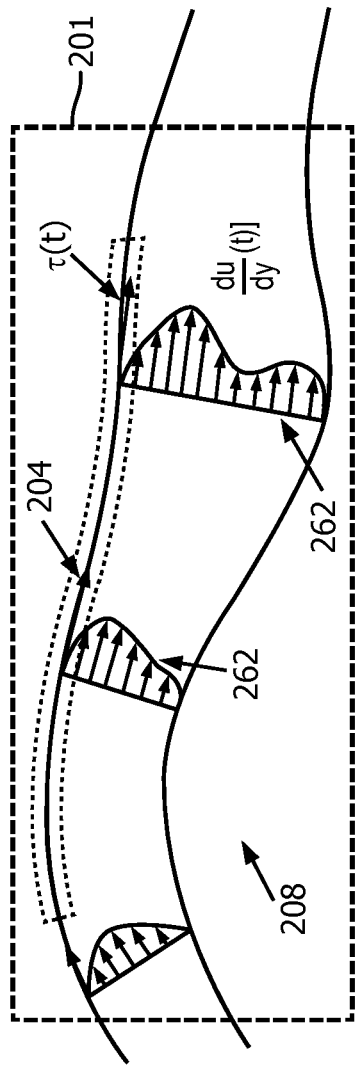
FIG. 3A is a diagrammatic illustration of a bodily structure and velocity profiles which may vary along the length of the bodily structure.
Figure 3B:
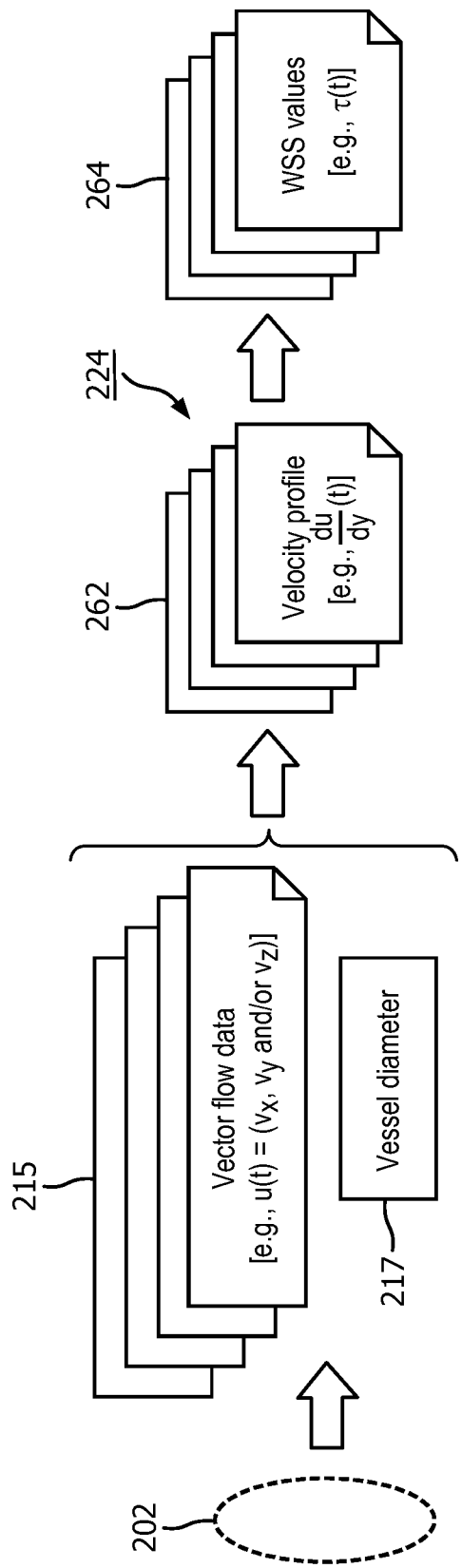
FIG. 3B is a diagrammatic illustration of processing steps that may be performed in a system or method in accordance with the present disclosure.

Referring now also to FIGS. 2-3, further aspects of the present invention are described. FIG. 2 shows another example of a system 200 according to the present disclosure which may include a processor 203 and a display unit 252. The processor 203 may include or be communicatively coupled with B-mode processor 205, which is configured to generate background grayscale images for concurrent display with the vector flow data and/or WSS visualization data, as described herein. The processor 203 may be coupled to a source of ultrasound imaging data. For example, the ultrasound imaging data 202 may be received (e.g., in real-time) from an ultrasound imaging apparatus responsive to ultrasonically scanning a region of interest 201. In some examples, the processor 203 may be coupled to a data storage device 207 (e.g., memory of an ultrasound imaging apparatus or PACS), e.g., for retrieval of previously-acquired ultrasound imaging data and/or storage of ultrasound images generated in accordance with the examples herein.

As described, the processor 203 may be configured to generate vector field data 215 which includes angle-independent velocity estimates (e.g., axial, lateral and/or elevational velocity components of the fluid flowing within the bodily structure) of the fluid flowing within the bodily structure. To that end, processor 203 may include a velocity vector estimator 210, which is configured to estimate axial, lateral and/or elevational velocity components in accordance with any suitable technique, several of which have been developed and described in the literature. For example, ultrafast Doppler imaging (e.g., using plane wave imaging) may be performed at sufficiently high pulse repetition frequency (PRF) in order to obtain sufficiently high frame rates to enable velocity vector estimation. Velocity vector estimates may be obtained in accordance with other known techniques such as multi-angle Doppler and Transverse Oscillation. At the end of the vector estimation process, frames 232 of vector field data may be generated and passed to a frame buffer 230. The vector field frame data 232 may be stored in the buffer 230 until it is accessed by the visualization processor 220 for generating visualization data 226. The frame buffer 230 may store frames of imaging data used at various stages of the visualization process, for example, frames of vector field data 215, frames of vector field visualization data (i.e., VFI data), and other types of visualization data (e.g., frames of WSS visualization data)

before the various types of visualization data is overlaid on background B-mode images for display.

The visualization processor 220 may be configured to generate different types of visualization and quantification data which provide spatiotemporal information about the bodily structure (e.g., vessel 208 in FIG. 3) and/or the fluid flowing therethrough. For example, the visualization processor 220 may receive frames of vector field data 215. The vector field data 215 may be coupled to a vector map processor 222 for generating a graphical representation of the vector field data (also referred to as herein as vector flow imaging data). The vector map processor 222 may produce frames of VFI data 226-1 (e.g., a velocity vector map), for example using pathlet-based or other type of vector flow visualization technique, and the VFI data 266-1 may be subsequently overlaid onto corresponding frames of B-mode image data for generating and displaying duplex or triplex mode images.

In accordance with the principles of the present invention, the visualization processor 220 may be further configured to extract quantitative information about the bodily structure from the angle-free velocity estimates. For example, the vector field data 215 may also be coupled to a wall shear stress (WSS) estimator 224, which may calculate WSS values along the wall of the bodily structure (e.g., vessel) and generate WSS visualization data 226-2, 226-3 from the calculated values. The WSS visualization data 226-2, 226-3 may be displayed concurrently (e.g., as an overlay and/or in a side-by-side arrangement) with the corresponding B-mode image, which may or may not include VFI data overlaid thereon. Using the velocity components, the WSS estimator 224 may calculate frames of WSS values at each of a plurality of locations along the wall of the bodily structure (e.g., vessel 208), in some cases along the entire length of the wall if the imaged structure. As noted, in some cases, WSS values are computed for each location along the length of the vessel wall. The vessel wall may be automatically identified by the processor 203, such as by segmentation of the flow and/or B-mode image data. In some embodiments, WSS values may be computed or displayed for only a portion of the vessel wall or for only select vessel walls (in the case of multiple vessels being present in the image) or portions thereof. In some embodiments, the processor 203 may be configured to provide WSS values for only a portion of the WSS ROI for example based on thresholding, which may identify the clinically relevant regions along the vessel wall(s) and leave out from the display other regions that are not deemed clinically relevant so as to reduce clutter in the displayed image. Thus, in examples herein, a WSS region of interest 204 may be defined, either automatically by the system, or based on user inputs. In the case of the latter, a user may specify the WSS ROI 204 for example by selecting, via a control panel 254, which may be provided as a touch sensitive display of the user interface 250, a plurality of points on a displayed image to trace the outline of the vessel wall and/or by drawing, via the user interface 250, the boundary of the WSS ROI 204.

After selecting the WSS ROI 204, the processor 203 may obtain a WSS distribution along the portion of the vessel wall within the WSS ROI 204. To achieve this, the WSS estimator 224 may calculate velocity gradients or profiles 262 across the vessel diameter. The velocity profiles capture the variations in velocity across the vessel diameter 217. The wall shear stress (τw), which is defined as the product of the fluid viscosity and velocity gradient, can then be computed according to the equation below:

$$\tau_W = \mu \frac{\partial u}{\partial y}\bigg|_{y=0}$$

in which μ is the dynamic viscosity of the fluid (e.g., blood), u is the velocity of the fluid along the wall, and y is the distance from the wall. WSS values 264 for each frame of data is computed. The spatiotemporal data may be passed through a spatiotemporal filter to smooth the results.

Figure 4:
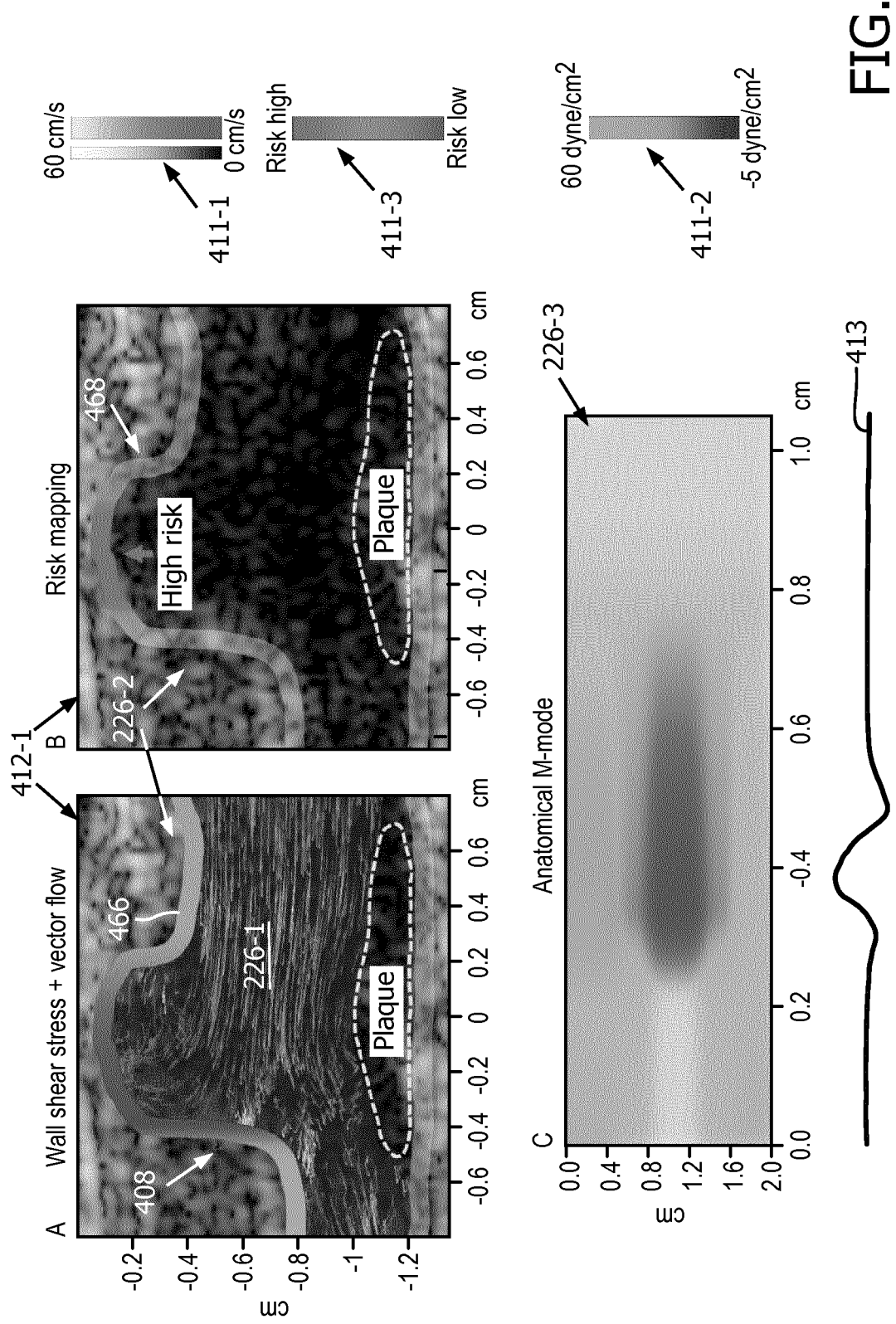
FIG. 4 shows a screen capture of images of a carotid artery which provide anatomical, flow, and wall shear stress information in accordance with the present disclosure.

In some embodiments, the processor 203 may be configured to encode in color a WSS value at each of the plurality of locations along the wall to generate the WSS visualization data. The WSS visualization data may be provided in the form of a color map which may be overlaid onto a grayscale image of the anatomy (i.e., an echo or B-mode image). This type of a displayed image (or simply display) may be referred to as a duplex mode image as it provides imaging data from two imaging modes, namely B-mode imaging and WSS imaging. For example, referring now also to FIG. 4, which shows images associated with vessel 408, in this case a portion of the carotid artery, the visualization processor 220 may generate WSS visualization data 226-2, 226-3 based, at least in part, on the calculated WSS values. The WSS visualization data 226-2, 226-3 may be displayed concurrently (e.g., as an overlay in the case of a color map, or adjacent thereto in the case of an M-mode display) with the B-mode image data 412-1. In some examples, the visualization processor 220 may color code the WSS values to produce a WSS color map 446 which shows the WSS distribution along the length of the vessel wall. The WSS color map 446 may be overlaid on the background B-mode image 412-1, as shown in FIG. 4. As will be understood, multiple frames of B-mode images and corresponding frames of WSS values may be generated and dynamically synchronously displayed as a temporal sequence (e.g., a cineloop), which may occur in real-time (e.g., while imaging the subject) or in a post-acquisition visualization session.

In some embodiments, the processor 203 may be also configured to generate a graphical representation of the vector field data 226-1 (e.g., a pathlet-based or other type of vector map) and cause the display unit (e.g., display unit 252) to display the graphical representation of the vector field data 226-1 concurrently with, for example as an overlay onto, the B-mode image 412-1, which may also include the WSS visualization data 262-2. This type of a displayed image (or simply display) may be referred to as a triplex mode image as it provides imaging data from three imaging modes, namely B-mode, vector flow imaging (VFI), and WSS imaging. An example of a triplex mode image is shown in FIG. 4, window A.

Another type of color map 262-2 that may be produced by visualization processor 220 may be a risk map (see color map 468 in FIG. 4). That is, in some embodiments, the WSS visualization data 262-2 may additionally or alternatively include risk values that are determined based, at least in part, on the calculated WSS values. For example, the processor 203 may be configured to estimate the plaque-development risk based, at least in part, on the calculated WSS values. Plaque-development risk estimates may be generated, in some examples, using a thresholding process. For example, the processor 203 may be configured to designate locations along the vessel wall that are associated with WSS values below a first or low WSS threshold (e.g., below 4 dyne/cm$^2$) as high-risk, and designate locations associated with WSS values above a second or regular WSS threshold (e.g., above 15 dyne/cm$^2$) as low-risk, while locations associated with WSS values between the high and low risk values are designed as medium risk. The processor 203 (namely visualization processor 220 in the example in FIG. 2), may color code the risk level to produce a risk color map 468. As shown in FIG. 4, window B, any location along the vessel wall that is associated with a low risk level is color coded in grey and any location that is associated with a high risk level is color coded in pink, with the intermediate risk levels color coded according to a color blend (e.g., a linear blend) between the threshold level colors. Window B of FIG. 4 shows a duplex type display in which a color map, in this case a risk map, is overlaid on the background B-mode image. While not specifically shown, it will be understood that a duplex mode display according to the present disclosure may include image data from any two types of imaging modes, e.g., any of the color maps (e.g., WSS color map or risk map) or the vector flow map 226-1 shown in window A. The image data associated with each imaging mode included in the displays may be dynamically and synchronously updated across all displayed images. In some examples, to preserve computational resources, the risk values may be assigned based on WSS values which are temporally-averaged over a certain number of frames, for example over the frames corresponding to the systolic phase of the cardiac cycle or over the entire cardiac cycle.

In some examples, the risk mapping may be enhanced by machine learning. For example, the processor 203 may be communicatively coupled to a neural network 270 trained to identify an appropriate low and regular WSS thresholds for the specific subject being scanned. The neural network 270 may be trained using training samples (e.g., prior patient screenings) from a diverse set of subjects that capture intra-patient and inter-patient variations, e.g., race, age, gender, etc. and other factors that may affect the WSS threshold definitions. The trained neural network 270 may then receive information about the subject (e.g., patient) being scanned and may identify the appropriate WSS thresholds, which are then communicated to the processor 203 for use in generating the risk map 468. Training samples may be retrieved from a data storage device (e.g., data storage 207 or the cloud).

In yet further examples, system 200 may be configured to provide additional spatiotemporal information based on the calculated WSS values. For example, the processor 203 may be further configured to generate a spatiotemporal plot which displays the WSS values along a portion or the full length of the vessel wall as a function of time, e.g., as shown in FIG. 4, window C. This type of display or image may be referred to as an anatomical or WSS M-mode display 226-3 or image. In the illustrated example M-mode display 226-3, the temporal dimension is shown on the x-axis and the spatial dimension (e.g., the location along the vessel wall) is shown on the y-axis. The WSS value at each location visualized in the M-mode may be color coded, for example using the same color coding relationship as used for the WSS color map, and the color coded values may be stitched together over a sequence of consecutive frames to form the M-mode display, as shown in FIG. 4, window C. The WSS M-mode display 226-3 may be provided concurrently (e.g., in a side-by-side arrangement) with any of the duplex or triplex mode images described herein, in which cases the WSS M-mode image may also be synchronously updated with the image data in the other displayed images.

In some cases, a cardiac cycle indicator 413 may accompany the WSS M-mode display or image 226-3. The cardiac cycle indicator 413 may be provided in the form of an ECG signal trace. To that end, the processor 203 may receive a concurrent ECG signal which may be measured using a conventional electrocardiograph. The ECG signal may be fed to the processor 203, which may generate an ECG signal trace for concurrent/synchronous display with the M-mode image. The ECG signal trace may be displayed adjacent to (e.g., below the time axis) of the M-mode image 226-3. With this additional image component, the characteristic events, including switch in WSS direction and peak WSS can be easily visualized thus providing rich spatiotemporal WSS information to the clinical that may enhance diagnostic efficiency.

The M-mode display 226-3 may be activated responsive to user input, e.g., via a software or hardware user control on the user interface 250. When the M-mode is active, the additional window displaying the M-mode image may be activated and color coded WSS values for the WSS ROI may be added in real-time to the plot to track the temporal variability of WSS during a cardiac cycle. In some examples, the system may enable the user to select a sub-region for the M-mode display, e.g., by clicking on two points along the wall to indicate the—spatial range for display or by selecting a single point and the system automatically determining a sub-region centered on the selected point. In some examples the temporal range for the M-mode display may be system-set to one cardiac cycle or the user may be provided with a control to select the temporal range and/or open the range for real-time tracking of the spatiotemporal distribution of WSS values in the selected sub-region.

Each type of visualization data is associated and accompanied with a color coding key. For example, as shown in FIG. 4, the multi-mode display may include a first color key 411-1 associated with the vector map 226-1, a second color key 411-2 which may be associated with the color encoding of WSS values (e.g., as used in the WSS color map 466 and also in the color coded M-mode display), and/or a third color key 411-3, which is associated with the color encoding of the risk map. In any of the examples herein, the image data from each mode in the overlay images (e.g., duplex or triplex mode images) may be synchronously dynamically updated in real time. For example, in the case of a duplex display, the B-mode image data may be displayed as a temporal sequence of a plurality of B-mode image frames, which may be acquired in real time or retrieved from memory (i.e., a cineloop) and the WSS visualization data (e.g., WSS color map) may also be displayed/overlaid as a temporal sequence of a plurality of corresponding WSS image data frames, which may be generated in real time (from real-time echoes) or retrieved from memory. Also, while specific examples are illustrated and described in the context of 2D imaging, it will be understood that the principles for quantifying and visualizing ultrasound imaging data may be equally applied to 3D imaging data. For example, the system 200 may further include a volume renderer 209, which may be operable to generate a 3D rendering of the anatomy (e.g., based on the B-mode image data) and the 3D rendering may be combined with 3D maps of the WSS values or risk values overlaid onto 3D regions within the rendered anatomy that correspond to the vessel walls. The combined 3D image 251, which in some examples may additionally and optionally include an overlay of a 3D vector flow map, may be provided to the user interface 250, e.g., for display on display unit 252.

As described, in some embodiments, the system may employ pathlet-based visualization for the graphical representation of the vector field data. FIGS. 5 and 6 illustrate examples of pathlet-based graphical representations of a vector field in accordance with some examples. While pathlet-based visualization is used to illustrate principles of the present invention, it will be understood that the visualization and quantification systems and methods described herein are not limited to pathlet-based visualization and can similarly be utilized with other vector flow imaging techniques, including but not limited to fixed-arrow based or free-arrow based visualization techniques.

The VFI data 226-1 may be provided in the form of a vector map 501, which may include a flow mask layer 505 delineating the flow region in a given color (e.g., dark red or another primary color) with a desired baseline transparency, for example 50%, so as to not completely obfuscate the background B-mode image 506. The vector map 501 may also include a vector field layer 507 illustrating the trajectories 509 of flow particles, which in this example are shown using pathlets.

In some embodiments, the flow region for which vector flow estimates are obtained and thus vector flow visualization performed may be user-defined, such as responsive to a user selection of a sub-region within the imaged ROI. In such embodiments, the size and shape of the flow mask layer 505 and correspondingly the vector field layer 507 are user-defined. This region selected by the user for vector flow visualization is not to be confused with the WSS ROI or sub-regions thereof, which are generally located along a vessel wall, while the flow region is generally defined to include an area within the vessel walls. In some embodiments, the flow region for which vector flow visualization is performed may be automatically defined by the system, e.g., example using image segmentation or other suitable image processing techniques such as to identify the walls of the vessel. In such embodiments, the system (e.g., by processor 203) may define the flow region to include the area inside an imaged vessel, and correspondingly a flow mask layer 505 and vector field layer 507 are produced for all points/pixels within the system-defined flow region.

In yet further embodiments, the flow region may be automatically defined by the system (e.g., by processor 203) based on available blood flow velocity data (i.e., based on points/pixels in the image which are associated with detected blood flow in any given frame). In such embodiments, the system may generate a flow mask layer 505 and corresponding vector field layer 507 for the system-defined flow region by including within the flow region all points/pixels in the image for which velocity estimates are available in any given frame. In such embodiments, the system (e.g., processor 203) may automatically update the vector flow image to reflect temporal variations in the blood flow velocity data. That is, as blood flow varies from frame to frame (e.g., responsive to the different phases of the cardiac cycle), the flow mask layer 505 corresponding vector field layer 507 may be dynamically updated from frame to frame to reflect this variation. Thus, the displayed vector field map may have a different shape or size in different frames. A combination of any of these or other suitable techniques may be used to define the flow region.

As described, pathlets for visualizing the vector field may be generated and updated in real-time (e.g., a frame of vector flow visualization data may be generated for each frame of image data) and overlaid on the flow mask to produce a vector flow image, which is then overlaid onto the corresponding B-mode image frame for display (e.g., on display unit 252). In this manner, e.g., by updating the pathlets in real time, the vector flow image may provide a visual cue of the movement of the tracked particles (e.g., blood flow). Each pathlet begins fading out when a distance from the tip exceeds a given threshold. That is, a head of the pathlet is always more opaque than the tail, enabling easier identification of the moving direction (i.e., flow direction) of the pathlet, even in a static image, without the inclusion of arrows that may clutter the display. Additionally, the pathlets may be color-coded and/or the pathlet length may be proportional to the velocity magnitude, both of these features helping the user more easily visualize the velocity magnitudes.

FIG. 6 shows partial magnified images of two consecutive frames 601 (i.e., frames N and N+1) of a pathlet-based vector map, which includes pathlets 603-1 and 603-2. The pathlets in the vector map, as well as the vector map generally, may be defined using several parameters, including length (alternatively, or additional and optionally, duration), width, and density of pathlets, generation rate of new pathlets (or alternatively vanish rate of old pathlets), color range for mapping of pathlets, display frame rate, and transparency and color of the flow mask, any of which parameters may be user-configurable (before or during imaging) to obtain a desired visualization effect without compromising the diagnostic performance of the system.

To generate the pathlets, initially a number of frames of the vector field data are saved and pathlets are generated for each frame, for example by interpolating the trajectory of tracked particles over the number of initial frames. For each subsequent frame, the pathlets are updated based on the velocity vector data associated with the subsequent frames. For example, in FIGS. 6A and 6B, the pathlets 603-1 and 603-2 illustrate the frontal portion of the trajectories of two tracked flow particles, the last several locations of one of which are shown by the points N+1, N, N−1, N−2, N−3, N−4, and N−5 which for illustration are so labeled to indicate the frame with which they are associated. The front most point in each frame indicates the estimated location of the tracked particle in that frame. The front most point of the pathlet in each frame (e.g., point N in frame N and point N+1 in frame N+1) is referred to as the head 605 of the pathlet. The pathlets may be updated every frame to reflect the movement of the particle to a new location and thus this movement may be visualized on the display by the changing location of the head 605 of the pathlet in each updated frame. The new location of the tracked particle and thus the head 605 is calculated using the angle-independent velocity estimates (i.e., the axial and lateral velocity components in the case of a 2D map or the axial, lateral and elevational velocity components in the case of a 3D map), which can be obtained in real-time or prior to the visualization. For example the axial displacement of the tracked particle may be calculated as $Vz/f_{FR}$ and the lateral displacement of the tracked particle may be calculated as $Vx/f_{FR}$, where Vx is the lateral velocity (m/s), Vz is the axial velocity (m/s) of the head, and $f_{FR}$ is the tracking frame rate (Hz). A continuous and smooth pathlet is generated by interpolation (linear or cubic) of these discrete dots, and then displayed as an aliasing-free line.

Overtime, the aft end of a particle's trajectory fades, e.g., to reduce clutter on the display, and only the frontal portion of the trajectory is shown on the display. The aft end of the displayed pathlet is referred to as the tail 607 of the pathlet. The pathlets (e.g., pathlets 603-1 and 603-2) may be color-coded based on the velocity magnitude at different locations (i.e., each segment 609 between the location of the particle in a previous frame and the location of the particle in the current frame may reflect the estimated velocity magnitude of the particle in the current frame). A color map key 411-1 (see FIG. 4) for the vector map may be displayed concurrently with the vector flow image. In addition to color-coding, the transparency of each pathlet may be linearly distributed with the highest opacity at the head 605 and decreasing to lowest opacity at the tail 607. The transparency distribution may also be updated at each frame. That is, when a new segment 609 is added in a new frame, the transparency may be linearly re-distributed with highest opacity (e.g., 50% or other) at the head 605 and decreasing to e.g., 100% transparency at the tail 607. The transparency may be linearly distributed, such as on a per pixel basis along the length of the pathlet or on a per segment basis. In this manner, the transparency distribution of the pathless may enhance the ease in identifying the direction of flow, even in a static image.

As previously described, each pathlet may have a maximum length, which may be pre-set or user defined. As the pathlet is updated frame to frame, it grows in length in each frame due to the addition of a new segment at the head while maintaining the same tail. Once the pathlet reaches its maximum length (e.g., after being updated certain number of frames), it maintains a length shorter than the maximum length by deletion of the oldest location of the particle and correspondingly the aft most segment (also referred to as tail segment). If the pathlet is further defined by duration, with each frame in which the pathlet is updated, a lifetime variable of the pathlet is incremented until the lifetime variable of a given pathlet reaches the maximum lifetime, at which point the pathlet is removed from the display. For example, alternatively or additionally, each pathlet may have a lifetime, which can be defined using an integer variable randomly generated between the maximum pathlet length and the maximum lifetime when the pathlet is created. The age of a pathlet is decrease by one for each frame (e.g., every time the pathlet is updated). Once the age reaches zero, the pathlet is deleted from the vector map. A new pathlet may be created at the same time or in a different frame with another random lifetime assigned to it. With this lifetime feature, a balanced spatial distribution of pathlets may be maintained. The pathlets may be updated using an iterative process for any subsequent frame. When the inputs (e.g., array variables including lateral position (x), axial position (z), lateral velocity $V_x$, and axial velocity ($V_z$), and two integer variables including "head of pathlet", and "lifetime of the pathlet") are received by the vector flow processor, the locations and lifetimes of the pathlets are examined. If a pathlet is located within the flow region, and its lifetime is greater than zero, it is defined as an active pathlet. If the pathlet moves outside of the flow region, or its lifetime is zero, it is defined as an inactive pathlet. For any active pathlets, the new head is computed based on the velocity maps, and the lifetime decreased by one. Any inactive pathlets are deleted from the display. An inactive pathlet may be replaced with a new pathlet for example, by randomly generating a new location and a new lifetime for the replacement pathlet. After the data structure for each pathlet is updated, the vector flow processor may generate (e.g., by interpolation) a smooth and continuous aliasing-free line to visualize the pathlets. The color of the line corresponding to each pathlet is coded based on the velocity magnitudes and the transparency of the color-coded pathlet is distributed along its length (i.e., from the new head to new tail of the pathlet) for rendering on the display.

Figure 8:
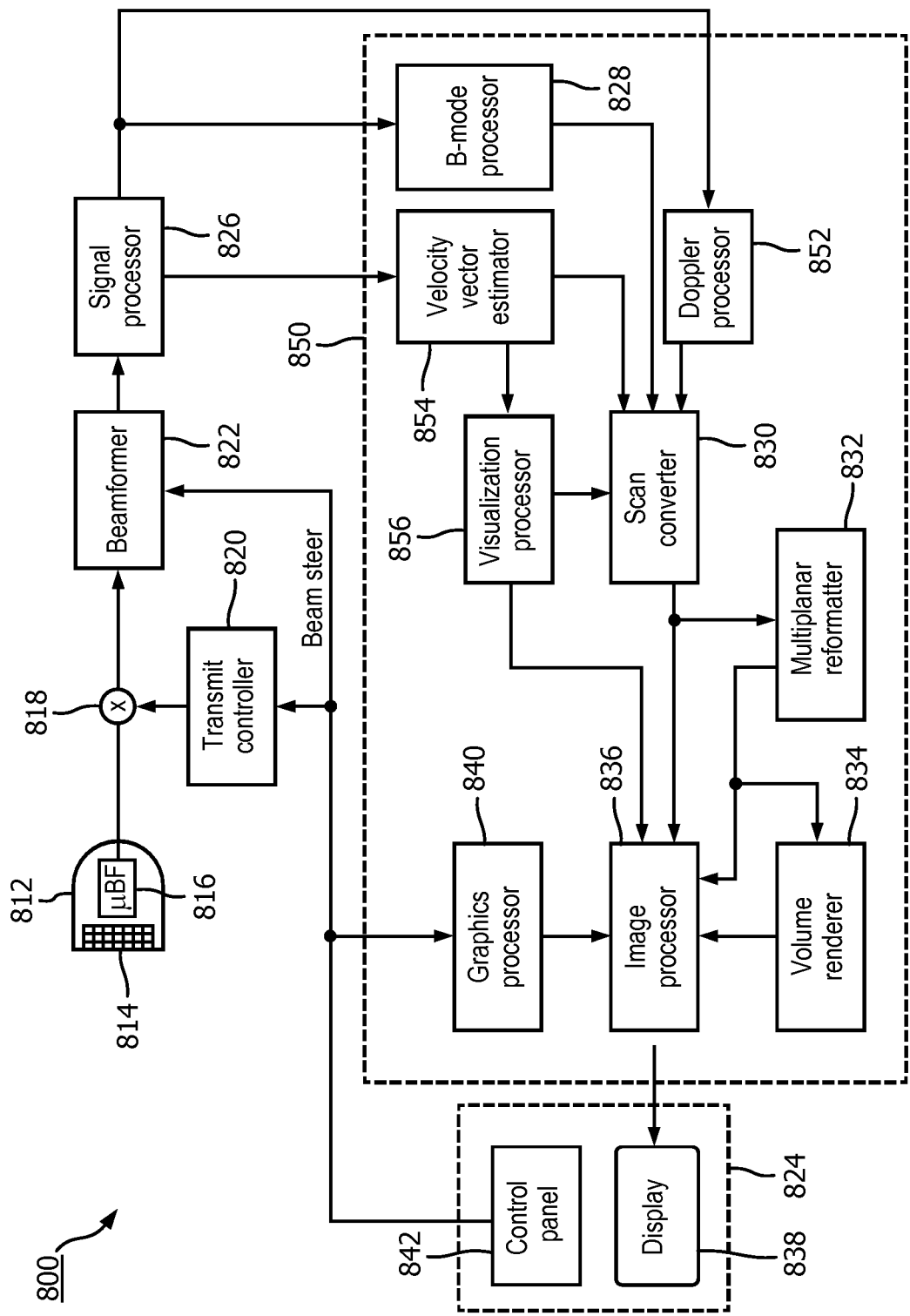
FIG. 8 shows a block diagram of an ultrasound imaging system in accordance with further examples of the present disclosure.

FIG. 8 shows a block diagram of an ultrasound system 800 according to the present disclosure. Some or all of the components of system 800 may be used to implement components of any one of the visualization and quantification systems described herein, for example the ultrasound imaging apparatus of FIG. 1. In some embodiments, the system 800 may include a processor (e.g., processor 850) and a display unit (e.g., display 838) in accordance with any of the examples described herein, for example as described with reference to FIG. 2. The ultrasound system 800 may include an ultrasound transducer array. In the illustrated example, the ultrasound transducer array 814 is provided in a probe 812. In some examples, the array 814 may be implemented using a plurality of patches, each comprising a sub-array of transducer elements and the array 814 may be configured to be conformably placed against the subject to be imaged. The array 814 is operable to transmit ultrasound toward a region of interest and to receive echoes for imaging the region of interest (ROI). A variety of transducer arrays may be used, e.g., linear arrays, curved arrays, or phased arrays. The array 814 may include, for example, a two dimensional array of transducer elements capable of scanning in both elevation and azimuth dimensions for 2D and/or 3D imaging.

The array 814 may be coupled to a microbeamformer, which may be located in the probe or in an ultrasound system base (e.g., in a cart-based system such as the SPARQ or EPIQ ultrasound system provided by Philips. The microbeamformer may control the transmission and reception of signals by the array. The array 814 may be coupled to the ultrasound system base via the microbeamformer 816, which may be coupled (via a wired or wireless connection) to a transmit/receive (T/R) switch 818 typically located in the base. The T/R switch 818 may be configured to switch between transmission and reception, e.g., to protect the main beamformer 822 from high energy transmit signals. In some embodiments, the functionality of the T/R switch 818 and other elements in the system may be incorporated within the probe, such as a probe operable to couple to a portable system, such as the LUMIFY system provided by PHILIPS. The probe 812 may be communicatively coupled to the base using a wired or wireless connection.

The transmission of ultrasonic pulses from the array 814 may be directed by the transmit controller 820 coupled to the T/R switch 818 and the beamformer 822, which may receive input from the user's operation of a user interface 824. The user interface 824 may include one or more input devices such as a control panel 842, which may include one or more mechanical controls (e.g., buttons, encoders, etc.), touch sensitive controls (e.g., a trackpad, a touchscreen, or the like), and other known input devices. Another function which may be controlled by the transmit controller 820 is the direction in which beams are steered. Beams may be steered straight ahead from (orthogonal to) the transmission side of the array 814, or at different angles for a wider field of view. The beamformer 822 may combine partially beamformed signals from groups of transducer elements of the individual patches into a fully beamformed signal. The beamformed signals may be coupled to a signal processor 826. The system 800 may include one or more processors (e.g., data and image processing components collectively referred to as processor 850) for generating ultrasound image data responsive to the echoes detected by the array 814, which may be provided in a system base. The processor 850 may be implemented in software and hardware components including one or more CPUs, GPUs, and/or ASICs specially configured to perform the functions described herein for generating ultrasound images and providing a user interface for display of the ultrasound images.

For example, the system 800 may include a signal processor 826 which is configured to process the received echo signals in various ways, such as by bandpass filtering, decimation, I and Q component separation, and harmonic signal separation. The signal processor 826 may also perform additional signal enhancement such as speckle reduction, signal compounding, and noise elimination. The processed signals may be coupled to a B-mode processor 828 for producing B-mode image data. The B-mode processor can employ amplitude detection for the imaging of structures in the body. The signals produced by the B-mode processor 828 may be coupled to a scan converter 830 and a multiplanar reformatter 832. The scan converter 830 may be configured to arrange the echo signals in the spatial relationship from which they were received in a desired image format. For instance, the scan converter 830 may arrange the echo signal into a two dimensional (2D) sector-shaped format, or a pyramidal or otherwise shaped three dimensional (3D) format. The multiplanar reformatter 832 can convert echoes which are received from points in a common plane in a volumetric region of the body into an ultrasonic image (e.g., a B-mode image) of that plane, for example as described in U.S. Pat. No. 6,443,896 (Detmer). A volume renderer 834 may generate an image of the 3D dataset as viewed from a given reference point, e.g., as described in U.S. Pat. No. 6,530,885 (Entrekin et al.).

Additionally or optionally, signals from the signal processor 826 may be coupled to a Doppler processor 852, which may be configured to estimate the Doppler shift and generate Doppler image data. The Doppler image data may include colorflow data which may be overlaid with B-mode (or grayscale) image data for displaying a conventional duplex B-mode/Doppler image. In some examples, the Doppler processor 826 may include a Doppler estimator such as an auto-correlator, in which velocity (Doppler frequency) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators. In some examples, the velocity and power estimates may undergo threshold detection to reduce noise, as well as segmentation and post-processing such as filling and smoothing. The velocity and power estimates may then be mapped to a desired range of display colors in accordance with a color map. The color data, also referred to as Doppler image data, may then be coupled the scan converter 830 where the Doppler image data is converted to the desired image format and overlaid on the B-mode image of the tissue structure containing the blood flow to form a color Doppler image.

In accordance with the principles of the present disclosure, the system 800 may include vector flow processing components which may be configured to perform the signal and image processing steps for quantifying and visualizing image data as described herein. For example, the vector flow processing components may include a velocity vector estimator 854 and a visualization processor 856. The velocity vector estimator may receive signals from the signal processor 826 and perform velocity estimation to obtain the angle-independent velocity vector data, as described herein. The velocity vector data (e.g., vector flow field) may be passed to a visualization processor 856 for generating graphical representations of the velocity vector data, including vector field visualization data and spatiotemporal data. Output (e.g., images) from the scan converter 830, the multiplanar reformatter 832, the volume renderer 834, and/or the visualization processor 856 may be coupled to an image processor 836 for further enhancement, buffering and temporary storage before being displayed on an image display 854. The system may include a graphics processor 840, which may generate graphic overlays for display with the images. These graphic overlays may contain, e.g., standard identifying information such as patient name, date and time of the image, imaging parameters, and other annotations. For these purposes, the graphics processor may be configured to receive input from the user interface 824, such as a typed patient name. Although shown as separate components, the functionality of any of the processors herein (e.g., the velocity vector estimator 854 and/or the visualization processor 856) may be incorporated into other processors (e.g., image processor 836 or volume renderer 834) resulting in a single or fewer number of discrete processing units. Furthermore, while processing of the echo signals, e.g., for purposes of generating B-mode images or Doppler images are discussed with reference to a B-mode processor and a Doppler processor, it will be understood that the functions of these processors may be integrated into a single processor, which may be combined with the functionality of the vector flow processing components.

Figure 9:
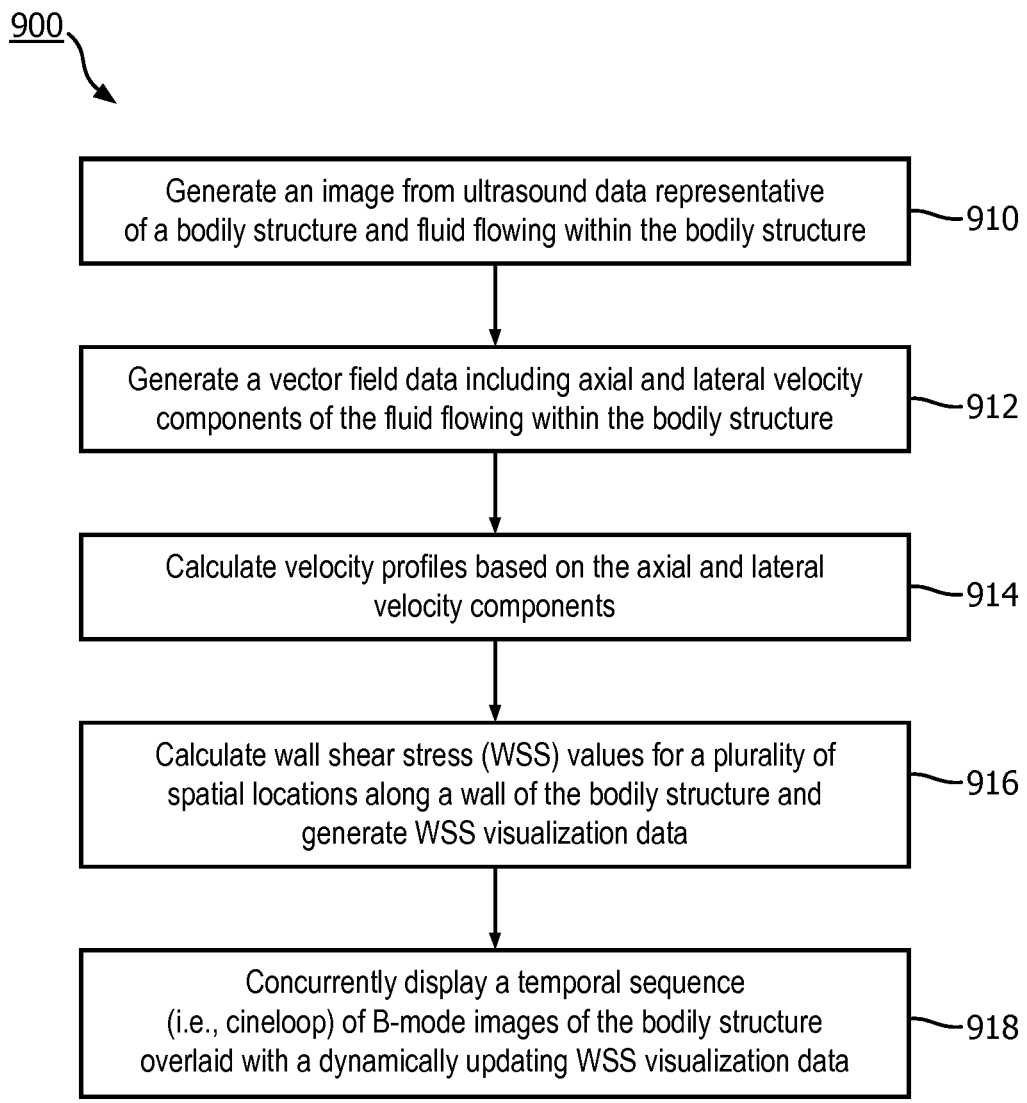
FIG. 9 is a flow diagram of a method for visualizing ultrasound imaging data in accordance with the present disclosure.

FIG. 9 is a flow diagram of an example method for quantification and visualization of ultrasound image data according to the present disclosure. The method 900 may include generating an image from ultrasound data representative of a bodily structure and fluid flowing within the bodily structure, as shown in block 910 in FIG. 9. The method 900 may further include generating vector field data including axial and lateral velocity components of the fluid flowing within the bodily structure, e.g., as shown in block 912. The method 900 may continue by calculating velocity profiles for a plurality of locations along a wall of the bodily structure based on the axial and lateral velocity components, as shown in block 914. Next, using the velocity profiles, WSS values may be calculated for the locations along the wall and wall shear stress (WSS) visualization data may be generated, as shown in block 916. In some embodiments of the method, the generating of WSS visualization data may include generating a color map of WSS values at each of the plurality of locations along the wall. In some embodiments, the generating of WSS visualization data may include generating a color map of risk estimates which may be based, at least in part, on the calculated WSS values. The method 900 may continue with concurrently displaying of an image including the bodily structure (e.g., B-mode image) with the WSS visualization data. In some embodiments, a temporal sequences (e.g., a cineloop) of the B-mode image data and WSS visualization data, e.g., as shown in block 918, to provide a rich dynamic display of spatiotemporal information.

In some embodiments, the WSS visualization data (e.g., color map of WSS values or risk estimates) is overlaid onto the B-mode image. In other embodiments, the WSS visualization data may be displayed adjacent to the B-mode image but nonetheless synchronized therewith. In some embodiments, WSS visualization data may be provided in the form of an M-mode image, as described herein. For example, the method may include displaying a graphical representation of the WSS values as a function of time, such as a color sequence of WSS values plotted as a function of time. In some embodiments, the graphical representation of the WSS values as a function of time may be displayed synchronously with a corresponding ECG signal trace. In embodiments according to the present disclosure, the image including the bodily structure (e.g., B-mode image) and the WSS visualization data may be updated in real-time. In yet further embodiments, the method may include generating a graphical representation of the vector field data such as a pathlet or arrow based visualization of the vector flow and the graphical representation of the vector field data may be concurrently displayed with the image including the WSS visualization data to provide a triplex mode display.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A system for visualization and quantification of ultrasound imaging data, the system comprising:
   a display unit;
   a neural network;
   a processor communicatively coupled to the display unit, the neural network, and to an ultrasound imaging apparatus for generating an image from ultrasound data representative of a bodily structure and fluid flowing within the bodily structure, wherein the processor is configured to:
   generate vector field data including axial and lateral velocity components of the fluid flowing within the bodily structure;
   calculate velocity profiles for a plurality of locations along a wall of the bodily structure based on the axial and lateral velocity components;
   generate wall shear stress (WSS) visualization data based, at least in part, on the velocity profiles, by encoding in color a WSS value at each of the plurality of locations wherein WSS visualization data comprises a color map of plaque-development risk estimates computed based, at least in part, on the WSS values and a threshold provided by the neural network; and
   cause the display unit to concurrently display the image including the bodily structure overlaid with the WSS visualization data.

2. The system of claim 1, wherein the processor is configured to automatically determine the plurality of locations associated with a length of the wall from the ultrasound imaging data.

3. The system of claim 1, wherein the processor is configured to select the plurality of locations associated with the wall responsive to user input.

4. The system of claim 1, wherein the WSS visualization data is displayed as an overlay on the image.

5. The system of claim 1, wherein the processor is further configured to generate a graphical representation of the vector field data and cause the display unit to display the graphical representation of the vector field data concurrently with the image including the WSS visualization data.

6. The system of claim 1, wherein the ultrasound imaging apparatus is provided by an ultrasound imaging system including the display and the processor, and wherein the ultrasound imaging system is configured to generate and update the B-mode image data and the WSS visualization data in real-time while ultrasonically imaging the bodily structure.

7. A system for visualization and quantification of ultrasound imaging data, the system comprising:
- a display unit;
- a processor communicatively coupled to the display unit and to an ultrasound imaging apparatus for generating an image from ultrasound data representative of a bodily structure and fluid flowing within the bodily structure, wherein the processor is configured to:
- generate vector field data including axial and lateral velocity components of the fluid flowing within the bodily structure;
- calculate velocity profiles for a plurality of locations along a wall of the bodily structure based on the axial and lateral velocity components;
- generate wall shear stress (WSS) visualization data based, at least in part, on the velocity profiles, by encoding in color a WSS value at each of the plurality of locations; and
- cause the display unit to concurrently display the image including the bodily structure overlaid with the WSS visualization data, wherein the WSS visualization data is displayed as an overlay on the image, and display a graphical representation of WSS values associated with some or all of the plurality of locations along the wall as a function of time.

8. A system for visualization and quantification of ultrasound imaging data, the system comprising:
- a display unit;
- a processor communicatively coupled to the display unit and to an ultrasound imaging apparatus for generating an image from ultrasound data representative of a bodily structure and fluid flowing within the bodily structure, wherein the processor is configured to:
- generate vector field data including axial and lateral velocity components of the fluid flowing within the bodily structure;
- calculate velocity profiles for a plurality of locations along a wall of the bodily structure based on the axial and lateral velocity components;
- generate wall shear stress (WSS) visualization data based, at least in part, on the velocity profiles, by encoding in color a WSS value at each of the plurality of locations;
- generate a graphical representation of the vector field data; and
- cause the display unit to concurrently display the image including the bodily structure overlaid with the WSS visualization data, the graphical representation of the vector field data concurrently with the image including the WSS visualization data, wherein the graphical representation of the vector field data is a pathlet-based visualization of the vector field data.

9. The system of claim 8, wherein the graphical representation of the vector field data comprises a vector map including a flow mask layer defining a sub-region corresponding to the vector field data and a vector visualization layer illustrating at least partial trajectories of velocity vectors of the vector field data.

10. A method for displaying ultrasound imaging data, the method comprising:
- generating an image from ultrasound data representative of a bodily structure and fluid flowing within the bodily structure;
- generating vector field data including axial and lateral velocity components of the fluid flowing within the bodily structure;
- calculating velocity profiles for a plurality of locations along a wall of the bodily structure based on the axial and lateral velocity components;
- generating wall shear stress (WSS) visualization data based, at least in part, on the velocity profiles, wherein the generating WSS visualization data includes generating a color map of WSS values at each of the plurality of locations along the wall;
- concurrently displaying the image including the bodily structure with the WSS visualization data; and
- generating a graphical representation of the vector field data; and concurrently displaying the graphical representation of the vector field data with the image including the bodily structure and the WSS visualization data, wherein the generating a graphical representation of the vector field data comprises generating a pathlet-based visualization of the vector field data.

11. The method of claim 10, and wherein the concurrently displaying the image with the WSS visualization data includes overlaying the color map of WSS values onto a B-mode image of the bodily structure.

12. The method of claim 10, wherein: the generating WSS visualization data includes calculating WSS values for each of the plurality of locations along the wall and generating a color map of risk estimates determined based, at least in part, on the WSS values; and the concurrently displaying the image with the WSS visualization data includes overlaying the color map of risk estimates onto a B-mode image of the bodily structure.

13. The method of claim 11, wherein the image including the bodily structure and the WSS visualization data are updated in real-time.

14. A method for displaying ultrasound imaging data, the method comprising:
- generating an image from ultrasound data representative of a bodily structure and fluid flowing within the bodily structure;
- generating vector field data including axial and lateral velocity components of the fluid flowing within the bodily structure;
- calculating velocity profiles for a plurality of locations along a wall of the bodily structure based on the axial and lateral velocity components;
- generating wall shear stress (WSS) visualization data based, at least in part, on the velocity profiles, wherein the generating WSS visualization data includes generating a color map of WSS values at each of the plurality of locations along the wall;
- concurrently displaying the image including the bodily structure with the WSS visualization data; and
- displaying a graphical representation of the WSS values as a function of time.

15. The method of claim 14, wherein the graphical representation of the WSS values as a function of time is displayed synchronously with a corresponding ECG signal trace.

16. A non-transitory computer-readable medium comprising executable instructions, which when executed cause a processor of medical imaging system to:

generate an image from ultrasound data representative of a bodily structure and fluid flowing within the bodily structure;
generate vector field data including axial and lateral velocity components of the fluid flowing within the bodily structure;
calculate velocity profiles for a plurality of locations along a wall of the bodily structure based on the axial and lateral velocity components;
generate wall shear stress (WSS) visualization data based, at least in part, on the velocity profiles, wherein the generating WSS visualization data includes generating a color map of WSS values at each of the plurality of locations along the wall;
concurrently display the image including the bodily structure with the WSS visualization data; and
display a graphical representation of the WSS values as a function of time.

* * * * *